(12) United States Patent
Handelsman et al.

(10) Patent No.: US 7,115,753 B2
(45) Date of Patent: Oct. 3, 2006

(54) TRIARYL CATION ANTIBIOTICS FROM ENVIRONMENTAL DNA

(75) Inventors: Jo E. Handelsman, Madison, WI (US); Robert M. Goodman, Madison, WI (US); Doreen E. Gillespie, Madison, WI (US); Alan D. Bettermann, Madison, WI (US); Jon C. Clardy, Ithaca, NY (US); Sean F. Brady, Ithaca, NY (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/637,280

(22) Filed: Aug. 8, 2003

(65) Prior Publication Data

US 2004/0034088 A1    Feb. 19, 2004

Related U.S. Application Data (60) Division of application No. 09/791,961, filed on Feb. 23, 2001, now abandoned, which is a continuation-in-part of application No. 09/558,712, filed on Apr. 26, 2000, now abandoned.

(51) Int. Cl.
C07D 209/16 (2006.01)
(52) U.S. Cl. .................. 548/506; 548/469; 548/484; 548/504
(58) Field of Classification Search ................ 435/108; 548/469, 506
See application file for complete search history.

(56) References Cited

U.S. PATENT DOCUMENTS 5,578,572 A * 11/1996 Horwitz et al. ................ 514/12

OTHER PUBLICATIONS

Oclarit, J. M.; Ohta, s.; Kamimura, K.; Yamaoka, Y.; Shimizu, T.; Ikegami, S. "A Novel Antimicrobial Substance form a Strain of the Bacterium, Vibrio Sp." Natural Product Letters 1994, 4, 309-312.*
Patan, G. A.; Lavoie, E. J. "Bioisosterism: A Rational Approach in Drug Design" Chem. Rev. 1996, 96,3147-3176.*
Altschul et al., (1990). Basic local allignment search tool. J. Mol. Biol. 215, 403-410.
Bintrim et al., (1997). Molecular phylogeny of Archaea from soil. Proc. Natl. Acd. Sci. U.S.A. 94, 277-282.
Borneman et al., (1996). Molecualr microbial diversity of an agricultural soil in Wisconsin. Appl. Environ. Microbiol. 62, 1935-1943.
Britschgi et al., (1991). Phylogenic analysis of a natural marine bacterioplankton population by rRNA gene cloning and sequencing, Appl. Environ. Microbiol. 57, 1707-1713.
Budzikiwicz et al., (1972). Bis (3-indolyl-)-3H-indolyliden-methan, em von. Saccharomyces Cerevisiae Gebildeter Farbstoff Tetrahedron Lett. 36, 3807-3810 (No translation provided).
Change et al., (1997), Cloning and sequence analysis of a novel hemolysin gene (v11Y) from Vibrio vulnificus. Appl. Environ. Microbiol. 63, 3851-3857.
Dhingra et al., (1985). Basic plant pathology methods. Boca Raton, FL: CRC Press, Inc., p. 308.
Fernandez-Canon et al., (1995). Molecular characterization of a gene encoding a homogentisate dioxygenase from Aspergillus nidulans and identification of its human and plant homologues. J. Biol. Chem. 270, 21199-21205.
Fuqua et al., (1991). Characterization of melA: a gene encoding melanin biosynthesis from the marine bacterium Shewanella colwellian. Gene, 109, 131-136.
Gibson et al., (1998). Melanin and novel precursots from Aeromonas media. FEMS Microbio. Lett. 169, 261-28, (and references therein).
Handelsman et al., (1998). Molecular biological access to the chemistry of unknown soil microbes: a new frontier for natural products. Chem. Biol. 5, R245-R249.
Hugenholtz et al., (1998). Impact of culture-independent studies on the emerging phylodenetic view of bacterial diverstiy. J. Bacteriol. 180, 4765-4774.
Kudo et al., (199). Molecualr and phylogenetic identification of the intestinal anaerobic microbioal communityin the termite, Reticulitermes spermatus, without cultivation. Extremophiles 2, 151-161.
Liesack et al., (1992). Occurence of novel groups of the domain Bacteria as revealed by analysis of genetic material isolated from an Australian terrestrial environment. J. Bacteriol. 174, 5072-5078.
Milcamps et al., (1999). Identification of a novel nutrient-deprivationinduced Sinorhizobium meliloti gene (hmgA) involved in the degradationof tyrosine.Microbiology 145, 935-947.
Redenbach et al., (1996). A set of ordered cosmids and a detailed genetic and physical map for the 8 Mb Streptomyces coelicolor A3(2) chromosome.Mol.Microbiol. 21, 77-96.
Rondon et al., (2000). Cloning the soil metagenome: a strategy for accessing the genetic and functional diversity of uncultured microorganisms. Appl. Environ. Microbiol., 66 in press.

(Continued)

*Primary Examiner*—Anrew Wang
*Assistant Examiner*—Jon D. Epperson
(74) *Attorney, Agent, or Firm*—Joseph T. Leone, Esq.; DeWitt Ross & Stevens S.C.

(57) ABSTRACT

Disclosed are triaryl cationic compounds that exhibit broad spectrum antibiotic and antifungal activity, pharmaceutical compositions containing the compounds, and methods of treating bacterial and fungal infections using the compounds. The compounds were initially isolated by screening a 25,000-member bacterial artificial chromosome (BAC) library of environmental (eDNA) from soil. At least one clone produced a dark brown melanin-like compound that was found to have antibiotic activity. The compounds were isolated and synthesized de novo. From within the positive clone, a single open reading frame that shares extensive sequence similarity with members of the 4-hydroxyphenylpyruvate family of enzymes was found to be necessary and sufficient to confer the production of at least one of the subject compounds on E. coli.

5 Claims, 2 Drawing Sheets

OTHER PUBLICATIONS

Saiki et al., (1988). Primer-directed enzymatic amplification of DNA with a thermostable DNA polymerase. *Science* 239, 487-491.

Sambrook et al., (1989). *Molecular Cloning: A Laboratory Manural*. (2ndd ed.), Cold Spring Harbor Laboratory Press, Cold Spring Harbor, NY. (Complete Book, copy not provided).

Schmidt et al.,. (1996). The use of diethylaminoethylcellulose membrane filters in a bioassay to quantify melanin synthesis. *Anal. Biochem.* 235, 113-118.

Shizuya et al.,(1992). Cloning and stable maintenance of 300-kilobase-pair fragments of human DNA in *Escherichia coli* using an F-factor-based vector. *Proc. Natl. Acad. Sci. U.S.A.* 89, 8794-8797.

Stackbrandt et al., (1993). Bacterial diversity in a soil sample from a subtropical Australian environment as determined by 16S rDNA analysis. *FASEB J.* 7, 232-236.

Stupnikova et al., (1978). Tris(3-indoyl)methyl perchlorates as new dyes of the triarylmethane series. Khim. Geterotsikl. Soedin. 3, 416-418 (No translation provided).

Suau et al., (1999). Direct analysis of genes encoding 16S rRNA from complex communities reveals many novel molecular species within the human gut. *Appl. Environ. Microbiol.* 65, 4799-4807.

Torsvik et al., (1990). High diversity of DNA of soil bacteria. *Appl. Environ. Microbiol.* 56, 782-787.

Torsvik et al., (1990). Comparison of phenotypic diversity and heterogeneity in a population of soil bacteria. *Appl. Environ. Microbiol.* 56, 776-781.

Ward et al., (1990). 16S rRNA sequences reveal numerous uncultured microorganisms in a natural community . *Nature* 345, 63-65.

Wintermeyer et al., (1994). Sequence determination and mutational analysis of the Ily locus of Legionella pneumophila. *Infect. Immun.* 62, 1109-1117.

Zhou et al., (1996). DNA recovery from soils of diverse composition. *Appl. Environ. Microbiol.* 62, 316-322.

* cited by examiner

FIG. 1

```
1    MQN--LPA-GTKGFDFLEFTTTKPRVLEQ---QFLSMGFVPVAKHNSIDITIYQQNDIRFIINADKNTLA   eDNA ORF1
1    MQN--NNPCGLDGFAFLEFSGPDRNKLHQ---QFSEMGFQAVAHHKNQDITLFKQGEIQFIVNAASHCQA   Lly
1    MVDAINPL-GTDGFEFVEYTAADNTGIEQLKHLFSSLGFAEVAKHRSKEAWLYRQGDINFVVNAQPHSQA   Vlly
1    ADLYENPM-GLMGFEFIELASPTPNTLEP---IFEIMGFTKVATHRSKDVHLYRQGAINLILNNEPHSVA   4HPPD
1    MASEQNPL-GLLGIEFTEFATPDLDFMHK---VFIDFGFSKLKKHKQKDIVYYKQNDINFLLNNEKQGFS   MelA 65   HQFAEQHGPSVSAMGFLVESAEDAYQYAITHGAQSYRPTQEVVPYTMPAIQGVGGSLIYFVD-YKQGKAN   eDNA ORF1
66   EAHASTHGPGACAMGFKVKDAKAAFQHAIAHGGIAFQDAPHANH-GLPAIQAIGGSVIYFVD-EEH----   Lly
70   EEFAKVHGPSVCGMAFRVQDAASALKHALTNGAEEYKTEIGPMELSIPAVYGIGGSLLYFVDRYGK----   Vlly
67   SYFAAEHGPSVCGMAFRVKDSQKAYKRALELGAQPIHIETGPMELNLPAIKGIGGAPLYLIDRFGE----   4HPPD
67   AQFAKTHGPAISSMGWRVEDANFAFEGAVARGAKPAADEV--KDLPYPAIYGIGDSLIYFIDTFGD----   MelA 134  YLQH---------FS---VLPTASAVKNAGLTYIDHVTHNLHRGNMNQWAEFYENIFNFKEVRYFDIEGR   eDNA ORF1
130  --QP---------FSHEWNITSPEPVVGNGLTAIDHLTHNVYRGNMDKWASFYASIFNFQEIRFFNIKGK   Lly
136  --QS-IYDVDFRFYD---DAAQRLAKSDVGLYEIDHLTHTLKRRNMDTWAGSMSVLVISVKIRYFDIERK   Vlly
133  --GSSIYDIDFVFLE---GVDRHPVGA--GLKIIDHLTHNVYRGRMAYWANFYEKLFNFREIRYFDIKGE   4HPPD
131  --DNNIYTSDF---E---ALDEPIITQEKGFIEVDHLTNNVHKGTMEYWSNFYKDIFGFTEVRYFDIKGS   MelA 192  LTGLKSRAMTSPCGKIRIPLNE-SSDDKSQIEEFLKDFNGEGIQHIALGTNDIYESVAQLHTKGLEFLDT   eDNA ORF1
189  MTGLVSRALGSPCGKIKIPLNE-SKDDLSQIEEFLHEYHGEGIQHIALNTNDIYKTVNGLRKQGVKFLDV   Lly
200  LTGLVSRAMNAPCGKIRIPINE-SSDDKSQIEEFIREYNGEGIQHIALTTDDIYQTVQTLRDRGMDFMPT   Vlly
196  YTGLTSKAMTAPDGMIRIPLNEESSKGAGQIEEFLMQFNGEGIQHVAFLSDDLIKTWDHLKSIGMRFMTA   4HPPD
193  QTALISYALRSPDGSFCIPINEGKGDDRNQIDEYLKEYDGPGVQHLAFRSRDIVASLDAMEGSSIQTLDI   MelA 261  PET-YYDLIEKRLPKHGESVERLRKNRILIDGTTETERK----ILLQIFTKNMLGPVFFEIIQRKGDEGF   eDNA ORF1
258  PDT-YYEMINDRLPWHKEPLNQLHAEKILIDGEADPKDG----LLLQIFTENIFGPVFFEIIQRKGNQGF   Lly
269  PDT-YYDKVDSRVEGHKENVSRLRDLRILIDGAP-LKDG----ILLQIFTQTVIGPVFFEIIQRKGNEGF   Vlly
266  PPDTYYEMLEGRLPNHGEPVGELQARGILLDGSS---ESGDKRLLLQIFSETLMGPVFFEFIQRKGDDGF   4HPPD
263  IPE-YYDTIFEKLPQVTEDRDRIKHHQILVDGDE---DG----YLLQIFTKNLFGPIFIEIIQRKNNLGF   MelA 326  GEGNPKALFESIELDQIKRGVLQVEQS   eDNA ORF1
323  GEGNFQALFEAIERDQVRRGTLK-ELS   Lly
333  GEGNFKALFESIEEDQIRRGVL--NNA   Vlly
333  GEGNFKALFESIERDQVRRGVL--STD   4HPPD
325  GEGNFKALFESIERDQVRRGVL        MelA
```

FIG. 2

SEQUENCE LISTING

```
<160> NUMBER OF SEQ ID NOS: 5

<210> SEQ ID NO 1
<211> LENGTH: 350
<212> TYPE: PRT
<213> ORGANISM: Unknown
<220> FEATURE:
<223> OTHER INFORMATION: DNA isolated from environmental samples
      containing uncultured microorganism
<220> FEATURE:
<221> NAME/KEY: orf_1
<222> LOCATION: (1)..(350)

<400> SEQUENCE: 1

Met Gln Asn Leu Pro Ala Gly Thr Lys Gly Phe Asp Phe Leu Glu Phe
1               5                   10                  15

Thr Thr Thr Lys Pro Arg Val Leu Glu Gln Gln Phe Leu Ser Met Gly
                20                  25                  30

Phe Val Pro Val Ala Lys His Asn Ser Ile Asp Ile Thr Ile Tyr Gln
            35                  40                  45

Gln Asn Asp Ile Arg Phe Ile Ile Asn Ala Asp Lys Asn Thr Leu Ala
        50                  55                  60

His Gln Phe Ala Gln His Gly Pro Ser Val Ser Ala Met Gly Phe Leu
65                  70                  75                  80

Val Glu Ser Ala Glu Asp Ala Tyr Gln Tyr Ala Ile Thr His Gly Ala
                85                  90                  95

Gln Ser Tyr Arg Pro Thr Gln Glu Val Val Pro Tyr Thr Met Pro Ala
            100                 105                 110

Ile Gln Gly Val Gly Gly Ser Leu Ile Tyr Phe Val Asp Tyr Lys Gln
        115                 120                 125

Gly Lys Ala Asn Tyr Leu Gln His Phe Ser Val Leu Pro Thr Ala Ser
    130                 135                 140

Ala Val Lys Asn Ala Gly Leu Thr Tyr Ile Asp His Val Thr His Asn
145                 150                 155                 160

Leu His Arg Gly Asn Met Asn Gln Trp Ala Glu Phe Tyr Glu Asn Ile
```

```
                    165                 170                 175
Phe Asn Phe Lys Glu Val Arg Tyr Phe Asp Ile Glu Gly Arg Leu Thr
            180                 185                 190

Gly Leu Lys Ser Arg Ala Met Thr Ser Pro Cys Gly Lys Ile Arg Ile
            195                 200                 205

Pro Leu Asn Glu Ser Ser Asp Lys Ser Gln Ile Glu Glu Phe Leu
            210                 215                 220

Lys Asp Phe Asn Gly Glu Gly Ile Gln His Ile Ala Leu Gly Thr Asn
225                 230                 235                 240

Asp Ile Tyr Glu Ser Val Ala Gln Leu His Thr Lys Gly Leu Glu Phe
                245                 250                 255

Leu Asp Thr Pro Glu Thr Tyr Tyr Asp Leu Ile Glu Lys Arg Leu Pro
            260                 265                 270

Lys His Gly Glu Ser Val Glu Arg Leu Arg Lys Asn Arg Ile Leu Ile
            275                 280                 285

Asp Gly Thr Thr Glu Thr Glu Arg Lys Ile Leu Leu Gln Ile Phe Thr
            290                 295                 300

Lys Asn Met Leu Gly Pro Val Phe Phe Glu Ile Ile Gln Arg Lys Gly
305                 310                 315                 320

Asp Glu Gly Phe Gly Glu Gly Phe Lys Ala Leu Phe Glu Ser Ile Glu
                325                 330                 335

Leu Asp Gln Ile Lys Arg Gly Val Leu Gln Val Glu Gln Ser
            340                 345                 350

<210> SEQ ID NO 2
<211> LENGTH: 348
<212> TYPE: PRT
<213> ORGANISM: Legionella pneumophila

<400> SEQUENCE: 2

Met Gln Asn Asn Pro Cys Gly Leu Asp Gly Phe Ala Phe Leu Glu
1               5                   10                  15

Phe Ser Gly Pro Asp Arg Asn Lys Leu His Gln Gln Phe Ser Glu Met
            20                  25                  30

Gly Phe Gln Ala Val Ala His His Lys Asn Gln Asp Ile Thr Leu Phe
        35                  40                  45

Lys Gln Gly Glu Ile Gln Phe Ile Val Asn Ala Ala Ser His Cys Gln
    50                  55                  60

Ala Glu Ala His Ala Ser Thr His Gly Pro Gly Ala Cys Ala Met Gly
65                  70                  75                  80

Phe Lys Val Lys Asp Ala Lys Ala Ala Phe Gln His Ala Ile Ala His
                85                  90                  95

Gly Gly Ile Ala Phe Gln Asp Ala Pro His Ala Asn His Gly Leu Pro
            100                 105                 110

Ala Ile Gln Ala Ile Gly Gly Ser Val Ile Tyr Phe Val Asp Glu Glu
        115                 120                 125

His Gln Pro Phe Ser His Glu Trp Asn Ile Thr Ser Pro Glu Pro Val
    130                 135                 140

Val Gly Asn Gly Leu Thr Ala Ile Asp His Leu Thr His Asn Val Tyr
145                 150                 155                 160

Arg Gly Asn Met Asp Lys Trp Ala Ser Phe Tyr Ala Ser Ile Phe Asn
                165                 170                 175

Phe Gln Glu Ile Arg Phe Phe Asn Ile Lys Gly Lys Met Thr Gly Leu
            180                 185                 190
```

-continued

```
Val Ser Arg Ala Leu Gly Ser Pro Cys Gly Lys Ile Lys Ile Pro Leu
        195                 200                 205

Asn Glu Ser Lys Asp Asp Leu Ser Gln Ile Glu Glu Phe Leu His Glu
        210                 215                 220

Tyr His Gly Glu Gly Ile Gln His Ile Ala Leu Asn Thr Asn Asp Ile
225                 230                 235                 240

Tyr Lys Thr Val Asn Gly Leu Arg Lys Gln Gly Val Lys Phe Leu Asp
                245                 250                 255

Val Pro Asp Thr Tyr Tyr Glu Met Ile Asn Asp Arg Leu Pro Trp His
                260                 265                 270

Lys Glu Pro Leu Asn Gln Leu His Ala Glu Lys Ile Leu Ile Asp Gly
            275                 280                 285

Glu Ala Asp Pro Lys Asp Gly Leu Leu Leu Gln Ile Phe Thr Glu Asn
        290                 295                 300

Ile Phe Gly Pro Val Phe Phe Glu Ile Ile Gln Arg Lys Gly Asn Gln
305                 310                 315                 320

Gly Phe Gly Glu Gly Asn Phe Gln Ala Leu Phe Glu Ala Ile Glu Arg
                325                 330                 335

Asp Gln Val Arg Arg Gly Thr Leu Lys Glu Leu Ser
            340                 345
```

<210> SEQ ID NO 3
<211> LENGTH: 356
<212> TYPE: PRT
<213> ORGANISM: Vibrio vulnificus

<400> SEQUENCE: 3

```
Met Val Asp Ala Ile Asn Pro Leu Gly Thr Asp Gly Phe Glu Phe Val
1               5                   10                  15

Glu Tyr Thr Ala Ala Asp Asn Thr Gly Ile Glu Gln Leu Lys His Leu
                20                  25                  30

Phe Ser Ser Leu Gly Phe Ala Glu Val Ala Lys His Arg Ser Lys Glu
            35                  40                  45

Ala Trp Leu Tyr Arg Gln Gly Asp Ile Asn Phe Val Val Asn Ala Gln
        50                  55                  60

Pro His Ser Gln Glu Glu Phe Ala Lys Val His Gly Pro Ser Val Cys
65                  70                  75                  80

Gly Met Ala Phe Arg Val Gln Asp Ala Ala Ser Ala Leu Lys His Ala
                85                  90                  95

Leu Thr Asn Gly Ala Glu Glu Tyr Lys Thr Glu Ile Gly Pro Met Glu
            100                 105                 110

Leu Ser Ile Pro Ala Val Tyr Gly Ile Gly Gly Ser Leu Leu Tyr Phe
        115                 120                 125

Val Asp Arg Tyr Gly Lys Gln Ser Ile Tyr Asp Val Asp Phe Arg Phe
    130                 135                 140

Tyr Asp Asp Ala Ala Gln Arg Leu Ala Lys Ser Asp Val Gly Leu Tyr
145                 150                 155                 160

Glu Ile Asp His Leu Thr His Thr Leu Lys Arg Arg Asn Met Asp Thr
                165                 170                 175

Trp Ala Gly Ser Met Ser Val Leu Val Ile Ser Val Lys Ile Arg Tyr
            180                 185                 190

Phe Asp Ile Glu Arg Lys Leu Thr Gly Leu Val Ser Arg Ala Met Asn
        195                 200                 205

Ala Pro Cys Gly Lys Ile Arg Ile Pro Ile Asn Glu Ser Ser Asp Asp
    210                 215                 220
```

```
Lys Ser Gln Ile Glu Glu Phe Ile Arg Glu Tyr Asn Gly Glu Gly Ile
225                 230                 235                 240

Gln His Ile Ala Leu Thr Thr Asp Asp Ile Tyr Gln Thr Val Gln Thr
                245                 250                 255

Leu Arg Asp Arg Gly Met Asp Phe Met Pro Thr Pro Asp Thr Tyr Tyr
            260                 265                 270

Asp Lys Val Asp Ser Arg Val Glu Gly His Lys Glu Asn Val Ser Arg
        275                 280                 285

Leu Arg Asp Leu Arg Ile Leu Ile Asp Gly Ala Pro Leu Lys Asp Gly
    290                 295                 300

Ile Leu Leu Gln Ile Phe Thr Gln Thr Val Ile Gly Pro Val Phe Phe
305                 310                 315                 320

Glu Ile Ile Gln Arg Lys Gly Asn Glu Gly Phe Gly Glu Gly Asn Phe
                325                 330                 335

Lys Ala Leu Phe Glu Ser Ile Glu Glu Asp Gln Ile Arg Arg Gly Val
            340                 345                 350

Leu Asn Asn Ala
        355

<210> SEQ ID NO 4
<211> LENGTH: 357
<212> TYPE: PRT
<213> ORGANISM: Pseudomonas sp.

<400> SEQUENCE: 4

Ala Asp Leu Tyr Glu Asn Pro Met Gly Leu Met Gly Phe Glu Phe Ile
1               5                   10                  15

Glu Leu Ala Ser Pro Thr Pro Asn Thr Leu Glu Pro Ile Phe Glu Ile
            20                  25                  30

Met Gly Phe Thr Lys Val Ala Thr His Arg Ser Lys Asp Val His Leu
        35                  40                  45

Tyr Arg Gln Gly Ala Ile Asn Leu Ile Leu Asn Asn Glu Pro His Ser
    50                  55                  60

Val Ala Ser Tyr Phe Ala Ala Glu His Gly Pro Ser Val Cys Gly Met
65                  70                  75                  80

Ala Phe Arg Val Lys Asp Ser Gln Lys Ala Tyr Lys Arg Ala Leu Glu
                85                  90                  95

Leu Gly Ala Gln Pro Ile His Ile Glu Thr Gly Pro Met Glu Leu Asn
            100                 105                 110

Leu Pro Ala Ile Lys Gly Ile Gly Gly Ala Pro Leu Tyr Leu Ile Asp
        115                 120                 125

Arg Phe Gly Glu Gly Ser Ser Ile Tyr Asp Ile Asp Phe Val Phe Leu
    130                 135                 140

Glu Gly Val Asp Arg His Pro Val Gly Ala Gly Leu Lys Ile Ile Asp
145                 150                 155                 160

His Leu Thr His Asn Val Tyr Arg Gly Arg Met Ala Tyr Trp Ala Asn
                165                 170                 175

Phe Tyr Glu Lys Leu Phe Asn Phe Arg Glu Ile Arg Tyr Phe Asp Ile
            180                 185                 190

Lys Gly Glu Tyr Thr Gly Leu Thr Ser Lys Ala Met Thr Ala Pro Asp
        195                 200                 205

Gly Met Ile Arg Ile Pro Leu Asn Glu Glu Ser Ser Lys Gly Ala Gly
    210                 215                 220

Gln Ile Glu Glu Phe Leu Met Gln Phe Asn Gly Glu Gly Ile Gln His
```

```
                      225                 230                 235                 240
Val Ala Phe Leu Ser Asp Asp Leu Ile Lys Thr Trp Asp His Leu Lys
                245                 250                 255
Ser Ile Gly Met Arg Phe Asn Thr Ala Pro Pro Asp Thr Tyr Tyr Glu
            260                 265                 270
Met Leu Glu Gly Arg Leu Pro Asn His Gly Glu Pro Val Gly Glu Leu
        275                 280                 285
Gln Ala Arg Gly Ile Leu Leu Asp Gly Ser Ser Glu Ser Gly Asp Lys
    290                 295                 300
Arg Leu Leu Leu Gln Ile Phe Ser Glu Thr Leu Met Gly Pro Val Phe
305                 310                 315                 320
Phe Glu Phe Ile Gln Arg Lys Gly Asp Asp Gly Phe Gly Glu Gly Asn
                325                 330                 335
Phe Lys Ala Leu Phe Glu Ser Ile Glu Arg Asp Gln Val Arg Arg Gly
            340                 345                 350
Val Leu Ser Thr Asp
        355

<210> SEQ ID NO 5
<211> LENGTH: 346
<212> TYPE: PRT
<213> ORGANISM: Shewanella colwelliana

<400> SEQUENCE: 5

Met Ala Ser Glu Gln Asn Pro Leu Gly Leu Gly Ile Glu Phe Thr
1               5                   10                  15
Glu Phe Ala Thr Pro Asp Leu Asp Phe Met His Lys Val Phe Ile Asp
                20                  25                  30
Phe Gly Phe Ser Lys Leu Lys Lys His Lys Gln Lys Asp Ile Val Tyr
            35                  40                  45
Tyr Lys Gln Asn Asp Ile Asn Phe Leu Leu Asn Glu Lys Gln Gly
    50                  55                  60
Phe Ser Ala Gln Phe Ala Lys Thr His Gly Pro Ala Ile Ser Ser Met
65                  70                  75                  80
Gly Trp Arg Val Glu Asp Ala Asn Phe Ala Phe Glu Gly Ala Val Ala
                85                  90                  95
Arg Gly Ala Lys Pro Ala Ala Asp Glu Val Lys Asp Leu Pro Tyr Pro
            100                 105                 110
Ala Ile Tyr Gly Ile Gly Asp Ser Leu Ile Tyr Phe Ile Asp Thr Phe
        115                 120                 125
Gly Asp Asp Asn Asn Ile Tyr Thr Ser Asp Phe Glu Ala Leu Asp Glu
    130                 135                 140
Pro Ile Ile Thr Gln Glu Lys Gly Phe Ile Glu Val Asp His Leu Thr
145                 150                 155                 160
Asn Asn Val His Lys Gly Thr Met Glu Tyr Trp Ser Asn Phe Tyr Lys
                165                 170                 175
Asp Ile Phe Gly Phe Thr Glu Val Arg Tyr Phe Asp Ile Lys Gly Ser
            180                 185                 190
Gln Thr Ala Leu Ile Ser Tyr Ala Leu Arg Ser Pro Asp Gly Ser Phe
        195                 200                 205
Cys Ile Pro Ile Asn Glu Gly Lys Gly Asp Asp Arg Asn Gln Ile Asp
    210                 215                 220
Glu Tyr Leu Lys Glu Tyr Asp Gly Pro Gly Val Gln His Leu Ala Phe
225                 230                 235                 240
```

```
Arg Ser Arg Asp Ile Val Ala Ser Leu Asp Ala Met Glu Gly Ser Ser
            245             250                 255

Ile Gln Thr Leu Asp Ile Ile Pro Glu Tyr Tyr Asp Thr Ile Phe Glu
            260             265                 270

Lys Leu Pro Gln Val Thr Glu Asp Arg Asp Arg Ile Lys His His Gln
            275             280                 285

Ile Leu Val Asp Gly Asp Glu Asp Gly Tyr Leu Leu Gln Ile Phe Thr
            290             295                 300

Lys Asn Leu Phe Gly Pro Ile Phe Ile Glu Ile Ile Gln Arg Lys Asn
305             310             315                 320

Asn Leu Gly Phe Gly Glu Gly Asn Phe Lys Ala Leu Phe Glu Ser Ile
            325             330                 335

Glu Arg Asp Gln Val Arg Arg Gly Val Leu
            340             345
```

TRIARYL CATION ANTIBIOTICS FROM ENVIRONMENTAL DNA

CROSS-REFERENCE TO RELATED APPLICATIONS

This is divisional of application Ser. No. 09/791,961, filed Feb. 23, 2001 (and now abandoned), which is a continuation-in-part of application Ser. No. 09/558,712, filed Apr. 26, 2000 (and now abandoned), the entirety of both of which are incorporated herein by reference.

FIELD OF THE INVENTION

The invention relates to antibiotics derived from microorganisms. In particular, the invention relates to antibiotic compounds having a triaryl-substituted methane core, pharmaceutical compositions containing the same, and methods of making the same.

BIBLIOGRAPHIC CITATIONS

Complete bibliographic citations to the references discussed herein are contained in the Bibliography section, directly preceding the claims.

BACKGROUND OF THE INVENTION

Cultured microorganisms produce an extraordinary array of structurally diverse and useful organic compounds. Molecular diversity measurements of microbial communities show that cultured microflora represent only a small fraction of the microbial diversity present in any natural environment. Currently unculturable microorganisms undoubtedly produce potentially valuable compounds and general methods to access these compounds are needed. An approach to study the natural products produced by uncultured microorganisms by introducing large fragments of DNA extracted directly from environmental samples (eDNA) into *E. coli* is described in co-pending parent application Ser. No. 09/558,712, filed Apr. 26, 2000. Heterologous expression of eDNA in an easily cultured host will provide access to the genomes of many uncultured microorganisms while bypassing the need to culture these organisms.

Natural products have traditionally been a rich source of small organic compounds that have found multiple uses in our daily lives. From the earliest known dyes and intoxicants to the most recent anti-neoplastic agents, natural products have been used by all human societies. The large collection of organic compounds that have been characterized from microbial sources is now known to have arisen from only a small sample of the earth's microbial diversity. Nucleic acids-based studies suggest that only a tiny fraction of any natural microbial community is cultured using standard microbiological methods. Uncultured bacteria have now been identified in a number of different environments including marine (1), gut (2, 3), hot springs (4), and soil (5, 6, 7). Uncultured microorganisms, therefore, represent one of the largest remaining unstudied pools of biodiversity. However, because these organisms are resistant to culturing, the natural products they produce remain inaccessible.

Using cloning and heterologous expression of large fragments of microbial DNA extracted directly from environmental samples (environmental DNA, eDNA) provides a means to access this previously untapped biodiversity. This approach has been termed "cloning the metagenome" to refer to accessing the collective genomes of the organisms in an environment (8). With the advent of bacterial cloning vectors such as the bacterial artificial chromosome (BAC), a vector that faithfully replicates very large fragments of DNA (9), it is now possible to clone and express in easily cultured hosts eDNA that codes for natural products produced by uncultured microorganisms. In short, direct cloning of eDNA provides a means to access the biosynthetic capacity of the genomes of heretofor uncultured microorganisms.

A metagenomics approach was first used to study the uncultured microflora present in soil samples. As with all other natural environments studied to date, the diversity of uncultured microorganisms in soil far exceeds that of cultured microorganisms. DNA-DNA reassociation kinetics and light microscopy analysis of soil samples indicate that cultured microorganisms represent less than 1% of the actual microbial diversity that exists in soil (10, 11). Analyzing small subunit rRNA gene sequences cloned from PCR-amplified soil DNA indicates that the uncultured microbial diversity in soil is much larger and more diverse than previously believed (5, 6, 7, 12). In addition to known examples of Archaea, Bacteria and Eukarya, analysis of small subunit rRNA gene sequences from soil microflora has consistently identified many sequences from previously uncharacterized microbial taxa. A recent analysis showed that nearly one third of the major divisions of phyla within the domain Bacteria are known only as environmental rRNA sequences (containing no cultivated members) and many of the well known divisions contain a wide diversity of as-yet-uncultivated members (13). Although there appears to be no easy way to culture this large collection of unstudied microorganisms, it is possible to isolate large fragments of microbial DNA directly from soil samples in high yields (>1 μg of DNA/gram of soil) (14, 15). The molecular diversity data from soil, together with the ease with which large eDNA can be harvested from soil samples, makes soil an ideal candidate for this new approach to the discovery of natural products.

Described herein are triaryl cationic antibiotics that are produced at elevated levels by a member of this library, pharmaceutical compositions containing the antibiotics, and methods of treating microbial infection using the pharmaceutical composition. The triaryl antibioutics were initially generated using a 25,000-member BAC library of eDNA extracted from soil (15; co-pending and co-owned U.S. patent application Ser. No. 09/558,712, filed Apr. 26, 2000), and subsequently synthesized de novo.

SUMMARY OF THE INVENTION

A first embodiment of the invention is directed to a pharmaceutical composition for treating microbial or fungal infections. The composition comprising an antibiotic-effective or an antifungal-effective amount of a compound having a structure as shown in Formula I or Formula II:

Formula I

Formula II

Each R group in the formulae is independently selected from the group consisting of hydrogen, halo, hydroxy, amino, unsubstituted $C_1$ to $C_6$-alkyl, and $C_1$ to $C_6$-alkyl substituted with one or more of halo, hydroxy, or amino. Expressly included within the scope of the invention are all stereo-isomers (i.e., individual isolated and/or enriched enantiomers or diasteromers, and racemic mixtures thereof) and pharmaceutically-acceptable salts thereof. The composition optionally is formulated in combination with a pharmaceutically-acceptable carrier. In the preferred embodiment, each R substituent is hydrogen or unsubstituted alkyl. The Formula I compound wherein each R is hydrogen has been given the trivial name turbomycin A; the Formula II compound wherein each R is hydrogen has been given the trivial name turbomycin B.

The composition displays antibiotic and antifungal activity and hence finds utility as a composition for the treatment of microbial and fungal infections. Thus, a second embodiment of the invention is drawn to treating bacterial or fungal infection in a subject in need thereof, the method comprising administering to the subject an antibiotic- or antifungal-effective amount of a compound of Formula I or Formula II. Such treatment expressly includes treatment of such infections in mammals, including humans.

A third embodiment of the invention is directed to novel compounds that exhibit antibiotic and antifungal activity. The compounds selected from the group consisting of:

Here, each R substituent in the Formula I structure is independently selected from the group consisting of hydrogen, halo, hydroxy, amino, unsubstituted $C_1$ to $C_6$-alkyl, and $C_1$ to $C_6$-alkyl substituted with one or more of halo, hydroxy, or amino, provided that each R group is not simultaneously hydrogen.

Each R' in the Formula II structure is independently selected from the group consisting of hydrogen, halo, hydroxy, amino, unsubstituted $C_1$ to $C_6$-alkyl, and $C_1$ to $C_6$-alkyl substituted with one or more of halo, hydroxy, or amino.

Expressly included within the scope of the recited compounds are all stereo-isomers (i.e., individual isolated and/or enriched enantiomers or diasteromers, and racemic mixtures thereof) and salts thereof. The preferred compound of Formula I has two R groups that are hydrogen, with the third R group being alkyl; the preferred compound of Formula II has all three R' groups being hydrogen.

A fourth embodiment of the invention is drawn to an isolated polypeptide that, when present in a microbe, results in the production by the microbe of compounds shown in Formulae I and II wherein each R (and/or R') is hydrogen. The isolated polypeptide is shown in SEQ. ID. NO. 1. The invention is also directed to an isolated polynucleotide that encodes the polypeptide as shown in SEQ. ID. NO. 1, and which drives the production of compounds of Formulae I and II wherein each R (and/or R') are hydrogen in microbes transformed to contain and express the polynucleotide.

Also described herein is the successful heterologous expression of eDNA extracted directly from soil as a means to access previously uncharacterized small organic compounds.

Further disclosed herein are methods for making the compounds of Formulae I and II. For example, to make a the compound of Formula I wherein all of the R substituents are hydrogen, a mixture of indole-3-carboxyaldehyde, indole, acetic acid, and ethanol is heated and neutralized to form a tri-substituted methane, which is subsequently oxidized. The oxidized substituted methane is then gently heated and the pH is increased. The resulting product is extracted to yield a crude reaction product containing the desired end product. The crude reaction product may then be further purified, if desired, by an number of means, such as by chromatography or recrystallization from an anti-solvent.

Compounds of Formula II can be made by an analogous method. For example, the compound of Formula II wherein each R substituent is hydrogen is made by heating a mixture of benzaldehyde, indole, acetic acid, and ethanol. The composition is neutralized to form a tri-substituted methane, which is then oxidized. The oxidized substituted methane is then heated and the pH is increased. The product can then be extracted an purified as noted herein.

A primary advantage of the invention is that it provides compounds and compositions effective to treat bacterial and fungal infections, including bacterial and fungal infections in humans. The infections that can be treated using the subjection compounds and compositions include, without limitation: *Erwinia herbicola, Escherichia coli, Salmonella typhimurium, Bacillus cereus, Bacillus subtilis, Staphylococcus aureus, Streptococcus pyogenes, Streptomyces griseus*, and *Candida guilliermondii*.

Another advantage of the present invention is that it provides a means to discover new compounds by direct cloning of eDNA taken from uncultured organisms. In short, the approach described herein demonstrates the feasibility and desirability of using direct cloning of eDNA to discover new compounds, including both new genes and their encoded polypeptides, and well as novel small organic molecules such as the novel antibiotic compounds described herein.

Further advantages, features, and objects of the invention will be apparent from the following detailed description of the invention in conjunction with the associated drawings.

BRIEF DESCRIPTION OF THE DRAWINGS

FIG. 2 depicts an alignment of ORFI with Lly (*L. pneumophila*) (ATCC No. Q53407), VllY (*V. vulnificus*) (ATCC No. 006695), 4HPPD (*Pseudomonas sp.*) (ATCC No. P80064), and MelA (*S. colwelliana*) (ATCC No. P23996). Identical base pairs are underlined.

DETAILED DESCRIPTION OF THE INVENTION

Initial Identifeation and Isolation of Compounds:

A 25,000-member bacterial artificial chromosome (BAC) library of eDNA from soil was screened for the production of colored compounds, and a clone, P57-G4, that produced a dark brown melanin like color was identified. The methanol extract of the acid precipitate from the culture broth of P57-G4 contained elevated levels of two triaryl, cationic compounds that were given the trivial names turbomycin A and B. (Turbomycin A is the compound of Formula I wherein all R groups are hydrogen; turbomycin B is the compound of Formula II wherein all R groups are hydrogen.) Both of turbomycin A and B were found to exhibit broad spectrum antibiotic activity. A single open reading frame within P57-G4 that shares extensive sequence similarity with members of the 4-hydroxyphenylpyruvate family of enzymes was necessary and sufficient to confer the production of color on *E. coi*. (For further discussion, see the Examples.)

$^{13}$C NMR spectra were recorded on a Varian Unity 400 spectrometer. $^{1}$H and two-dimensional spectra were recorded on a Varian Unity 500 spectrometer. $^{1}$H-$^{13}$C HMQC and $^{1}$H-$^{13}$C HMBC experiments were run using pulse field gradients. Mass spectral data were acquired.

To isolate the natural products from the culture broth, cell-free culture broth from P57-G4 grown in LB medium for 48 hours (37° C.) was brought to pH 13 with NaOH, stirred for one hour, and then acidified to pH 2 with HCl. Separate methanol extracts of the precipitate wer collected by filtration after 24 hours and 72 hours. Each extract as then resuspended in 80:20 chloroform:methanol and the chloroform:methanol solution was then passed over a silica plug to remove any remaining insoluble material.

The eluent from the silica plug was partitioned by silica gel chromatography using a chloroform:methanol step gradient modified with 0.2% acetic acid (95:5, 90:10, 80:20, and 0:100). The 90:10 fraction was dried, reapplied to a silica column and developed using a chloroform:methanol step gradient modified with 0.1% triethylamine (95:5, 90:10, 80:20, and 0:100). Fractions from both the 24 and 72 hour precipitates containing turbomycin A were pooled from the 80 to 90% chloroform eluent, while fractions containing turbomycin B were pooled from the 95% chloroform fluent. Turbomycin A ($R_f$0.39, silica gel TLC, chloroform:methanol:acetic acid, 80:20:0.2) was obtained from a final normal phase column (85:15 chloroform:methanol modified with 0.2% acetic acid). TurbomycinB ($R_f$0.73, silica gel TLC, chloroform:methanol:acetic acid, 80:20:0.2) was obtained from a final normal phase column (step gradient, 93:7 and 86:14 modified with 0.2% acetic acid).

NMR and mass spectrometry data (see also Table 1):

Turbomycin A: HRMS-FAB (m/z): (M)+calculated for $C_{25}H_{18}N_3$ 360.1501; found 360.1498; $^{1}$H NMR (500 MHz, CD$_3$OD referenced at 3.31 ppm) 8.15 (3H, s, H1, 1', 1"), 7.66 (3H, d, 10.5, H7, 7', 7"), 7.35 (3H, t, d 8.5, 2, H6, 6', 6"), 7.08 (3H, t, 9, H5, 5', 5"), 7.04 (3H, bd, 10, H4, 4', 4"); $^{13}$C NMR (100 MHz, CD$_3$OD referenced at 49.15 ppm) 143.1 (C2, 2', 2"), 121.3, (C3, 3', 3"), 128.3 (C3a, 3a', 3a"), 122.5 (C4, 4', 4"), 124.7 (C5, 5', 5"), 126.3 (C6, 6', 6"), 114.7 (C7, 7', 7"), 140.1 (C7a, 7a', 7a"), 163.1 (C8).

Turbomycin B: HRMS-FAB (m/z): (M)+calculated for C23H$_{17}$N$_2$ 321.1392 found 321.1389; $^{1}$H NMR (500 MHz, CD$_3$OD referenced at 3.31 ppm) 8.24 (2H, s, H2, 2'), 7.87 (m, H12), 7.68 (6H, m, H7, 7', 10, 14, 11, 13), 7.41 (2H, t, 7, H6, 6'), 7.25 (2H, t, 7, H5, 5'), 6.87 (2H, d, 8, H4, 4'); $^{13}$C NMR (100 MHz, CD$_3$OD referenced at 49.15 ppm) 147.8 (C2, 2'), 124.0 (C3, 3'), 128.3 (C3a, 3a'), 123.1 (C4, 4'), 125.8 (C5, 5'), 127.5 (C6, 6'), 115.5 (C7, 7'), 141.8 (C7a, 7a'), 171.4 (C8), 140.4 (C9), 130.6* (C10, 14), 134.7* (C11, 13), 135.0 (C 12)

*NMR assignment are ambiguous.

TABLE 1

$^1$H and $^{13}$C NMR data for Turbomycin A and B

| Turbomycin B | $^{13}C^a$ | $^1H^{b,c}$ | Turbomycin A | $^{13}C^a$ | $^1H^{b,c}$ |
|---|---|---|---|---|---|
| 1, 1', 1" | | NH | 1, 1' | | NH |
| 2, 2', 2" | 143.1 | 8.15 (3H, s) | 2, 2' | 147.8 | 8.24 (2H, s) |
| 3, 3', 3" | 121.3 | | 3, 3' | 124.0 | |
| 3a, 3a', 3a" | 128.3 | | 3a, 3a' | 128.3 | |
| 4, 4', 4" | 122.5 | 7.04 (3H, bd, 10) | 4, 4' | 123.1 | 6.87 (2H, d, 8) |
| 5, 5', 5" | 124.7 | 7.08 (3H, t, 9) | 5, 5' | 125.8 | 7.25 (2H, t, 7) |
| 6, 6', 6" | 126.3 | 7.35 (3H, t, d, 8.5, 2) | 6, 6' | 127.5 | 7.41 (2H, t, 7) |
| 7, 7', 7" | 114.7 | 7.66 (3H, d, 10.5) | 7, 7' | 115.5 | 7.68 (2H, m) |
| 7a, 7a', 7a" | 140.1 | | 7a, 7a' | 141.8 | |
| 8 | 163.1 | | 8 | 171.4 | |
| | | | 9 | 140.4 | |
| | | | 10, 14$^d$ | 130.6 | 7.68 (2H, m) |
| | | | 11, 13$^d$ | 134.7 | 7.68 (2H, m) |
| | | | 12 | 135.0 | 7.87 (m) |

$^a$referenced at 49.15 ppm in CD$_3$OD
$^b$referenced at 3.31 ppm in CD$_3$OD
$^c$assignments determined by $^1$H—$^{13}$C HMQC
$^d$assignment uncertain De Novo Synthesis of Turbomycin A and B:

Turbomycin A and B were made by heating 250 μmoles of the appropriate aldehyde (indole-3-carboxyaldehyde for turbomycin A and benzaldehyde for turbomycin B), 500 μmoles indole, 40 μl acetic acid, and 360 μl ethanol at 80° C. for 4 hours. The reaction was neutralized with 10% NaOH, and the tri-substituted methane oxidized in situ by adding 200 mg tetrachloro-1,4-benzoquinone and heating at 80° C. for 40 minutes. An equal volume of 10% NaOH was then added and the reaction extracted 3 times with ethyl acetate to obtain a crude reaction product.

Synthetic turbomycin A, spectroscopically identical to the natural product, was obtained from the crude indole-3-carboxyaldehyde reaction product following two normal phase chromatography steps (90:10:0.1 chloroform:methanol:triethylamine followed by 80:20:0.1 chloroform:methanol:acetic acid).

Synthetic turbomycin B, spectroscopically identical to the natural product, was obtained from the crude benzaldehyde reaction product following two normal phase chromatography steps (98:2:0.1 chloroform:methanol:triethylamine followed by 90:10:0.1 chloroform:methanol:acetic acid).

Synthesis of the substituted forms of the Formula I and II compounds is accomplished in the same fashion as described above, using an appropriately substituted indole-carboxyaldehydes to yield corresponding compounds of Formula I wherein one or more R groups is a substituent other then hydrogen and using an appropriately substituted benzaldehydes to yield corresponding compounds of Formula II wherein one or more R groups is a substituent other then hydrogen.

X-ray Crystal Structure Determination of Synthetic Product:

Synthetic turbomycin A was converted to the perchlorate salt and then crystallized from acetone and water by slow evaporation. An orange block crystal (0.50×0.40×0.30 mm$^3$) was mounted on a Bruker "SMART" diffractometer equipped with a 3KW sealed tube (MoK$_\alpha$) X-ray generator. The perchlorate salt of synthetic turbomycin B crystallized in the P1 bar space group with unit cell dimensions α=10.5517 (9) Å, b=10.8951 (9) Å, c=12.223 (1) Å. A hemisphere of data was taken using a narrow-frame method (1321 frames, 0.3°ω-scan, exposure time of 30 seconds/frame, 2θ$_{max}$=52.42°). Raw data were integrated with the Bruker "SAINT" program to yield a total of 6313 reflections, of which 4266 were independent (R$_{int}$=2.94%), and 3200 were above 4σ(F). Data were corrected for adsorption using the "SABABS" program. The structure was solved by direct methods and refined by full matrix least squares on F$^2$ techniques using anisotropic displacement parameters for all non-hydrogen atoms and hydrogen atoms were included in all calculated positions. At final convergence, R$_1$=8.79% and GOF=1.307 for 407 parameters. Archival data have been deposited with the Cambridge Crystallographic Data Center.

Genetic Manipulation of eDNA Required for Turbomycin Production:

Many of the steps noted herein for the manipulation of DNA, including digesting with restriction endonucleases, amplifying by PCR, hybridizing, ligating, separating and isolating by gel electrophoresis, transforming cells with heterologous DNA, selecting successful transformants, and the like, are well known and widely practiced by those skilled in the art and are not extensively elaborated upon herein. Unless otherwise noted, the DNA protocols utilized herein are described extensively in Sambrook, J.; Fritsch, E. F.; Maniatis, T. (1989), *Molecular Cloning: A Laboratory Manual*; Cold Spring Harbor Laboratory Press: New York, N.Y.

*E. coli* DH10B was used for all cloning and culturing. The library was constructed in pBeloBAC11, as previously described (15).

P57-G4 was digested with PstI and shotgun cloned into pGEM-5Zf+ (Promega, Madison, Wis.) following standard techniques (26). The "GPS-1" Genome Priming System (NEB; Beverly, Mass.) was used to generate transposon insertions according to the supplier's instructions. Donor plasmid and G4P8 were mixed at a X:X molar ratio, and transformants were selected on kanamycin/chloramphenicol.

DNA sequencing was performed on an ABI Model 377 automated sequencer. Sequence similarity searches were conducted using BLAST (27), and other analyses were conducted with "DNASTAR" software (Madison, Wis.).

Construction of a Clone Expressing Legiolysin:

To determine whether the legiolysin (lly) gene of *Legionella pneumophila* conferred the same activity in *E. coli* as the putative ORF1 sequence in G4P8 cloned from eDNA (the sequence that confers production of turbomycin A and B (see Examples), lly-specific primers were designed based on sequences in GenBank and used to amplify the lly coding sequences and upstream promoter regions according to standard protocols (28). The PCR product was cloned into the vector pGEM-T (Promega; Madison, Wis.) and electroporated into DH10B. Clones containing the lly gene were verified by restriction digestion and homogentisate-melanin pigment production.

Cell-free Assay for Turbomycin Production:

The potential interaction of homogentisate (HGA) (an intermediate in the tyrosine degradation pathway) and indole compounds in the formation of turbomycins in a cell-free assay was investigated by the incubation of HGA and indole compounds in growth conditions identical to those employed for the *E. coli* clones. A range of HGA, indole, and indole-3-carboxaldehyde concentrations (1 μM to 1 mM) were added to 10 ml LB medium, separately and in combination, followed by incubation at 37° C. in aerated 18-mm culture tubes for 48 hours. The cell-free media were then adjusted to pH 13 with NaOH, stirred for 1 hour, and acidified to pH 2 with HCl for 48 hours at room temperature. The dark brown precipitate was collected by filtration and then extracted with methanol. The methanol extract was then resolved by TLC as described above.

Zone of Inhibition Assays:

Organisms were streaked onto Brain Heart Infusion plates containing 5% yeast extract. *Escherichia coli* (H5997), *Staphylococcus aureus* (3001), *Enterococcus faecalis* (4025), *Streptococcus pyogenes* (8P01), and *Pseudomonas aeruginosa* (9020) were incubated at 37° C.; *Bacillus subtilis* (BR151pPL608), *Bacillus cereus* var. *mycoides* (1003), *Erwinia herbicola* (IRQ), *Salmonella typhimurium* (LT2), *Streptomyces griseus* (6501), and *Candida guilliermondii* (Y001) were incubated at 28° C. A single colony from each organism was inoculated into 10 ml of BHI broth in a 100 ml flask. All cultures were shaken at 200 rpm overnight (12 hours).

Screening plates were prepared by adding 200 µl of the overnight cultures to 20 ml of cooled medium (BHI/YE). Natural and synthetic turbomycin A and turbomycin B, dissolved in DMSO to a concentration of 250 µg/ml, were applied as 10 µl drops to the surface of the plate. The plates were placed at 4° C. overnight (12 hours), then incubated at either 37° C. or 28° C. until a lawn developed. Inhibition was scored visually and zones of inhibition reported as the diameter of the zone in millimeters. The assay was conducted in duplicate plates.

*Pythium ultimum* (1033) and *Fusarium solani* f sp. *glycine* (90.1) were grown on ¼- strength potato dextrose agar (29) at 23° C. Plugs were cut from the fungal lawn using a #5 cork borer and placed onto the center of a fresh plate containing the DMSO-dissolved compounds. The plates were incubated 7 days, or until the organism covered the plate, at 23° C., in the dark.

Minimum Inhibitory Concentration (MIC) Determination:

Overnight cultures were prepared as for the plate inhibition assays. Culture optical densities (O.D.) were normalized to 0.15 (150 µl path length) by performing 1:1 serial dilutions (150 µl transfer into 150 µl diluent) in a 96 well microtiter plate. Inoculum cell concentrations (colony forming units/ml) were subsequently determined by performing 1:5 serial dilution series (50 µl transfer into 200 µl diluent) in a second microtiter plate. Three dilutions were plated ($3.13 \times 10^3$, $1.56 \times 10^4$, $7.81 \times 10^5$) by mixing 50 µl of a given dilution into 20 ml of cooled BHI/YE medium and quickly pouring into a petri plate.

Test compounds, both natural and synthetic, were dissolved in DMSO (2.0 mg/ml) and diluted into BHI/YE medium to a concentration of 106 µg/ml (5.35% v/v DMSO). Samples of each of the test compounds (150 µl each) were added to 3 separate wells, each containing 150 µl of BHI/YE medium (no DMSO). Serial dilutions (1:1) were performed (150 µl transfer into 150 µl diluent containing 2.6% DMSO) to achieve final concentrations of 50, 25, 12.5, 6.25, 3.12, 1.56, and 0.78 µg/ml. Three plates were prepared for each test organism (n=3 reps/plate×3 plts=9 per compound, per organism). Additional wells were included in duplicate on each plate for color subtraction, +/−DMSO, and minus compound controls (n=2 reps/plate×3 plts=6 per control, per organism).

Ten µl of normalized inoculum was added per well. Absorbance at 590 nm was read using a Wallec Victor® Microtiter plate reader; double circular mixing was performed for 10 seconds prior to reading at times 0, 30 and 60 hours. The plates were statically incubated at 28° C. when not being read. Absorbance values were imported into Microsoft Excel® and analyzed graphically.

Utility:

The triaryl cationic compounds described herein, including the pharmaceutically-acceptable salts and isomeric forms thereof, have antibiotic and anti-fungal activity. Consequently, these compounds and pharmaceutical compositions containing the compounds are useful to prevent and to treat pathophysiological conditions due to, caused by, or mediated in whole or in part, by bacterial infection.

Pharmaceutical Compositions:

Another aspect of the invention provides pharmaceutical compositions, for medical use, comprising an active compound, i.e., a Formula I or II compound or a pharmaceutically-acceptable salt thereof, in combination with an acceptable carrier therefor and optionally with other therapeutically-active ingredients or inactive accessory ingredients. The carrier must be pharmaceutically-acceptable in the sense of being compatible with the other ingredients of the formulation and not deleterious to the recipient. The pharmaceutical compositions include those suitable for oral, topical, inhalation, rectal or parenteral (including subcutaneous, intramuscular and intravenous) administration.

The formulations may conveniently be presented in unit dosage form and may be prepared by any of the methods well known in the art of pharmacy. The term "unit dosage" or "unit dose" is denoted to mean a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as an aqueous solution, suspension, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine a mixture of the powdered active compound with any suitable carrier.

Formulations suitable for parenteral administration conveniently comprise a sterile preparation of the active compound in, for example, water for injection, saline, a polyethylene glycol solution and the like, which is preferably isotonic with the blood of the recipient.

Useful formulations also comprise concentrated solutions or solids containing the compound of Formula I or II which upon dilution with an appropriate solvent give a solution suitable for parenteral administration.

Preparations for topical or local applications comprise aerosol sprays, lotions, gels, ointments, suppositories etc., and pharmaceutically-acceptable vehicles therefore such as water, saline, lower aliphatic alcohols, polyglycerols such as glycerol, polyethylene glycerol, esters of fatty acids, oils and fats, silicones, and other conventional topical carriers. In topical formulations, the subject compounds are preferably utilized at a concentration of from about 0.1% to 10.0% by weight.

Compositions suitable for rectal administration, comprise a suppository, preferably bullet-shaped, containing the active ingredient and pharmaceutically-acceptable vehicles therefore such as hard fat, hydrogenated cocoglyceride, polyethylene glycol and the like. In suppository formulations, the subject compounds are preferably utilized at concentrations of from about 0.1% to 10% by weight.

Compositions suitable for rectal administration may also comprise a rectal enema unit containing the active ingredient and pharmaceutically-acceptable vehicles therefore such as 50% aqueous ethanol or an aqueous salt solution which is physiologically compatible with the rectum or colon. The rectal enema unit consists of an applicator tip protected by an inert cover, preferably comprised of polyethylene, lubricated with a lubricant such as white petrolatum and preferably protected by a one-way valve to prevent back-flow of the dispensed formula, and of sufficient length, preferably two inches, to be inserted into the colon via the anus. In rectal formulations, the subject compounds are preferably utilized at concentrations offrom about 5.0–10% by weight.

Useful formulations also comprise concentrated solutions or solids containing the active ingredient which upon dilution with an appropriate solvent, preferably saline, give a solution suitable for rectal administration. The rectal compositions include aqueous and non-aqueous formulations which may contain conventional adjuvants such as buffers, bacteriostats, sugars, thickening agents and the like. The compositions may be presented in rectal single dose or multi-dose containers, for example, rectal enema units.

Preparations for topical or local surgical applications for treating a wound comprise dressings suitable for wound care. In both topical or local surgical applications, the sterile preparations of compounds of Formula I or II are preferably utilized at concentrations of from about 0.1% to 5.0% by weight applied to a dressing.

Compositions suitable for administration by inhalation include formulations wherein the active ingredient is a solid or liquid admixed in a micronized powder having a particle size in the range of about 5 µm or less to about 500 µm or liquid formulations in a suitable diluent. These formulations are designed for rapid inhalation through the oral passage from a conventional delivery systems such as inhalers, metered-dose inhalers, nebulizers, and the like. Suitable liquid nasal compositions include conventional nasal sprays, nasal drops and the like, of aqueous solutions of the active ingredient(s).

In addition to the aforementioned ingredients, the formulations of this invention may further include one or more optional accessory ingredient(s) utilized in the art of pharmaceutical formulations, i.e., diluents, buffers, flavoring agents, colorants, binders, surface active agents, thickeners, lubricants, suspending agents, preservatives (including antioxidants) and the like.

The amount of compound of Formula I or II required to be effective for any indicated condition will, of course, vary with the individual subject being treated and is ultimately at the discretion of the medical or veterinary practitioner. The factors to be considered include the condition being treated, the route of administration, the nature of the formulation, the subject's body weight, surface area, age and general condition, and the particular compound to be administered. In general, a suitable effective dose is in the range of about 0.1 to about 500 mg/kg body weight per day, preferably in the range of about 5 to about 350 mg/kg per day, calculated as the non-salt form of Formula I or II. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

In general, the pharmaceutical compositions of this invention contain from about 0.5 mg to about 1.5 g active ingredient per unit dose and, preferably, from about 7.5 to about 1000 mg per per unit dose. If discrete multiple doses are indicated, treatment might typically be 100 mg of a compound of Formula I or II given from two to four times per day.

The antibacterial and anti-fungal compounds and compositions according to the present invention may be administered prophylactically, chronically, or acutely. For example, such compounds may be administered prophylactically to patients known to be prone to bacterial or fungal infections, or who are known to have been exposed to potentially infectious agents. The subject compounds may also be administered prophylactically to patients suffering other conditions, such as AIDS or other immune-system-suppressing conditions, that render them susceptible to opportunistic infections. In addition to the prevention of such infections, chronic administration of the subject compounds will typically be indicated in treating refractory conditions, such as persistent infection by multiple drug-resistant strains of bacterial or fungus. Acute administration of the subject compounds is indicated to treat, for example, those subjects presenting with classical indications of bacterial or fungal infection.

EXAMPLES

The following examples are provided for illustrative purposes only. It is understood that the following examples do not limit the invention claimed herein in any way.

BAC Library Construction:

The construction of the soil eDNA BAC library that was used to screen for the production of colored compounds has been described elsewhere (15; co-pending and co-owned U.S. patent application Ser. No. 09/558,712, filed Apr. 26, 2000,). eDNA was isolated directly from soil samples by a freeze-thaw cycle in lysis buffer, followed by extraction with phenol/chloroform and recovery from the aqueous phase by isopropanol precipitation. High molecular weight DNA was purified from the crude DNA samples by two successive pulsed field agarose gel purifications. Size-selected, partially digested high molecular weight DNA was then used to construct a 24,546 member BAC library of soil DNA in the pBeloBAC11 (9) vector. A colored clone from the library, designated P57-G4, was found to produce a dark brown/orange color when grown in LB medium. This discovery prompted a closer examination of the culture broth of this clone.

Characterization of the Acid Precipitate:

The presence of a dark brown color in bacterial cultures is generally characteristic of the production of melanin or a melanin-type polymer that can be collected from culture broth by acid precipitation. Upon acidification of the P57-G4 culture broth, a dark brown precipitate formed, suggesting the presence of melanin in the culture. The dark brown material in the acid precipitate harvested from the P57-G4 (like other bacterial melanin, see references 16, 17) was: 1)

insoluble in aqueous acid; 2) soluble in aqueous base; 3) adhered to an anion-exchange column (DEAE-cellulose); and 4) had a molecular weight of >7000 Daltons.

Antibiotic Isolation and Characterization:

The acid precipitate from P57-G4 cultures were examined for additional colored compounds that could be extracted with an organic solvent. Two colored compounds were extracted with methanol from the acid precipitate that formed when the cell-free culture broth of P57-G4 grown in LB for 48 hours (37° C.) was brought to pH 13 with NaOH, stirred for one hour and then acidified to pH 2 with HCl. Using normal phase chromatography, an orange (turbomycin A) and a red (turbomycin B) compound were isolated in approximately a 20:1 ratio from the methanol extract. Both compounds show broad-spectrum antibiotic activity as is demonstrated in Table 2.

TABLE 2

Antibiotic Activities of Synthetic and Natural Turbomycin A and B.

| Organisms and Strains | Turbomycin A | | Turbomycin B | |
|---|---|---|---|---|
| | Synthetic | Natural | Synthetic | Natural |
| Gram Negative | | | | |
| *Erwinia herbicola* IRQ | +[a] | + | + | + |
| *Escherichia coli* HS997 | +/−[b] | +/− | +/− | +/− |
| *Pseudomonas aeruginosa* 9020 | −[c] | − | − | − |
| *Salmonella typhimurium* LT2 | + | + | + | + |
| Gram Positive | | | | |
| *B. cereus* var. *mycoides* 1003 | + | + | + | + |
| *Bacillus subtilis* BR151pPL | + | + | + | + |
| *Enterococcus faecalis* 4025 | − | − | − | − |
| *Staphylococcus aureus* 3001 | + | + | + | + |
| *Streptococcus pyogenes* 8P01 | + | + | + | + |
| *Streptomyces griseus* 6501 | + | + | + | + |
| Fungi/Protists | | | | |
| *Candida guilliermondii* Y001 | +/− | +/− | +/− | +/− |
| *Pythium ultimum* 1033 | − | − | − | − |
| *Fusarium solani* (f. sp. *glycine*) 90.1 | − | − | − | − |

[a](+) 2 to 13 mm zone,
[b](+/−) 1 mm zone,
[c](−) no zone of inhibition.

In broth culture, the minimum inhibitory concentration (MIC) for synthetic turbomycin A was 6.2 μg/ml for *Erwinia herbicola, Bacillus subtilis, Staphylococcus aureus*, and *Streptococcus pyogenes*, and 12.5 μg/ml for *Salmonella typhimurium*. The natural product and synthetic compound were tested in the same experiment against *S. aureus* and had the same MIC.

Structure Determination:

HRFABMS data for turbomycin A (Formula I, each R is hydrogen) indicated a molecular formula of $C_{25}H_{18}N_3$, while 1- and 2-DNMR experiments suggested the presence of only 5 distinct proton environments and 9 distinct carbon environments. The ortho substituted aromatic ring of the indole was easily identified from the 4-carbon spin system seen in $^1H$-$^1H$ Relay H experiments and the nitrogen at position 1 was suggested by the deshielding of C-2, C-7a, and H-2. The remainder of a C-3 substituted indole was confirmed by $^1H$-$^{13}C$ HMBC correlations from C-3 a, -3, -7a and -8 to H-2. All 5 protons and 9 carbons observed by NMR are present in the C-3 substituted indole partial structure.

The structure of turbomycin B (Formula II, each R is hydrogen) was supported by the molecular formula deduced by HRFABMS. However, it was not possible to establish conclusively this structure using spectral data alone. Therefore, synthesis and single crystal X-ray diffraction analysis were used to confirm the structure shown in Formula II.

Synthetic turbomycin B was made by heating indole-3-carboxyaldehyde and indole in 10% acetic acid, and then oxidizing in situ with tetrachloro-1, 4-benzoquinone to yield an orange compound that was spectroscopically identical to the natural product. The structure of the synthetic material was confirmed by single crystal X-ray diffraction analysis of the perchlorate salt.

For turbomycin B, the presence of the indole was deduced in the same manner as described for turbomycin A and the para substitued phenol was apparent from both the $^1H$ NMR spectrum and the additional spin system observed in $^1H$-$^1H$ RelayH experiments. The structure shown in Formula II was suggested by the molecular formula predicted by HRFABMS, $C_{23}H_{17}N_2$. As with turbomycin A, the proposed structure of turbomycin B was confirmed by de novo synthesis: Benzaldehyde was heated with indole in 10% acetic acid and the resulting substituted methane was then oxidized in situ with tetrachloro-1,4-benzoquinone to yield a red compound that was spectroscopically identical to the compound isolated from the P57-G4 culture media.

Figure 1:
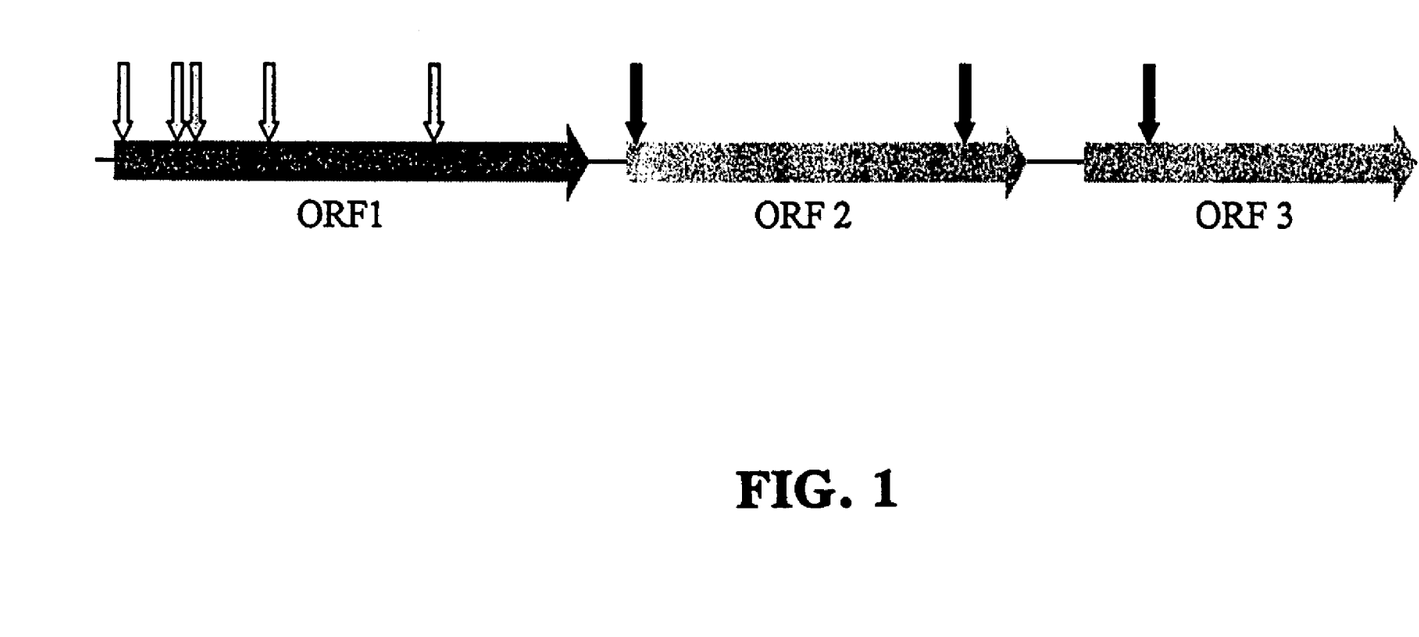
FIG. 1 illustrates ORFs and GPS transposon insertion sites in the eDNA subclone G4P8. Shaded arrows indicate transposon insertions that did not disrupt turbomycin A and B accumulation; unshaded arrows indicate insertions that resulted in the lack of turbomycin A and B accumulation.

Characterization of the Antibiotic Producing Clone:

The P57-G4 clone contains a 25-kb insert of eDNA. PstI fragments of P57-G4 were subcloned into pGEM-5Zf+ to generate templates for end sequencing. One of the subclones, G4P8, produced brown pigment when grown in liquid and on solid medium. TLC analysis of supernatant precipitates from P57-G4 and G4P8 cultures revealed that both turbomycin A and B were present in G4P8 cultures, indicating that the genetic information required for color production in P57-G4 cultures was present on the G4P8 subclone. G4P8 was found to contain a 3-kb insert entirely from the P57-G4 environmental insert DNA. Sequence analysis of this insert revealed three ORFs (FIG. 1).

The deduced protein encoded by ORF1 (SEQ. ID. NO. 1) shares extensive similarity with legiolysin (Lly) (SEQ. ID. NO. 2) from *Legionella pneumophila* (53% identity, 71% similarity), hemolysin (Vlly) (SEQ. ID. NO. 3) from *Vibrio vulnificus* (54% identity, 71% similarity) (20), 4-hydroxyphenylpyruvate dioxygenase (4HPPD) (SEQ. ID. NO. 4) from *Pseudomonas sp.* (49% identity, 67% similarity), and MelA (SEQ. ID. NO. 5) from *Shewanella colwelliana* (45% identity, 63% similarity) (21). FIG. 2 is an amino acid alignment of these sequences. Lly, hemolysin, MelA, and 4HPPD are considered to be members of the 4HPPD family and are believed to be components of the tyrosine/phenylalanine degradation pathway. Identical residues are underlined.

Translation and analysis of the remaining ORFs in G4P8 revealed predicted proteins containing similarity to other putative members of the tyrosine/phenylalanine degradation pathway. The deduced protein product of ORF2 contains weak similarity to an uncharacterized *Sinorhizobium meliloti* ORF. This ORF is found in the n4 locus of *S. meliloti* linked to other members of the tyrosine degradation pathway and is believed to be a potential member of that or a related pathway (22).

The deduced protein product of ORF3 contains similarity to a member of the maleylacetoacetate isomerase, which is responsible for the degradation of maleylacotacetate in the tyrosine degradation pathway.

End sequencing of additional PstI clones derived from subcloning of P57-G4 identified the neighboring coding sequence for ORF3 found on G4P8 and an adjacent sequence with homology to homogentisate deoxygenase (hmgA). Homogentisate (HGA) is an intermediate in the tyrosine degradation pathway and is also the polymerization substrate in *L. pneumophila* cultures. Homologs of hmgA have been identified in only two other non-eukaryotic species, *S. meliloti* (22) and *Streptomyces coelicolor* (23). Mutations in hmgA in *S. meliloti* result in the accumulation of a brown pigmentation, likely homogentisate or an analog (22). Similar observations have been made from cultures of *Aspergillus nidulans* carrying a mutation in its hmgA gene (24). In *L. pneumophila* and *S. cotwelliana*, expression of lly and melA, ORF1 homologs, results in the accumulation of HGA-melanin, a dark pigment generated by the spontaneous polymerization of phenolic compounds (25).

Clone G4P8 was mutagenized with transposon GPS-1, and the resulting mutants were screened for color production. The five non-color-producing insertion mutants all carried the transposon within the ORF1 coding sequence (FIG. 1). Of six color-producing insertion mutants, two carried an insertion in the vector, and four carried an insertion in non-vector sequences outside the ORF1 coding sequences. TLC analysis indicated that clones carrying insertions within ORF1 produced neither turbomycin A nor turbomycin B. These results indicate that ORF1 is necessary and sufficient for color production in *E. coli*.

The methanol extract from the uninoculated LB medium control, treated in the same manner as P57-G4 cultures, did not contain turbomycin A or B. However, the methanol extracts of the acid precipitate harvested from control cultures (*E. coli* transformed with the BAC vector containing no insert eDNA) contained very small quantities of both turbomycin A and B. The major colored metabolite, turbomycin A, however, was present in approximately 80-fold excess in the culture of P57-G4 compared to the BAC vector control.

The gene encoding legiolysin (lly), which is the gene most closely related to ORF1, was introduced into *E. coli*. Clones containing lly also produced a melanin-like brown pigment and had elevated levels of triaryl cations in the acid precipitate harvested from the culture broth, strongly suggesting that the formation of these types of triaryl compounds correlates with the presence of HGA-melanin in the culture medium.

Therefore, a cell-free system, containing HGA, was tested for the production of compounds of Formulae I or II. The addition of 1 mM HGA to LB medium resulted in the formation of significant quantities of HGA-melanin pigment by 48 hours. However, the formation of HGA-melanin from HGA (1 µM to 1 mM) in this cell-free system was not sufficient for the production of the orange or red pigments or the compounds of Formulae I or II.

BIBLIOGRAPHY

1. Britschgi, T. B. & Giovannoni, S. J. (1991). Phylogenic analysis of a natural marine bacterioplankton population by rRNA gene cloning and sequencing. Appl. Environ. Microbiol. 57, 1707–1713.
2. Suau, A., Bonnet, R., Sutren, M., Godon, J. J., Gibson, G. R., Bonnet, R., Malene, S. & Dore, J. (1999). Direct analysis of genes encoding 16S rRNA from complex communities reveals many novel molecular species within the human gut. Appl. Environ. Microbiol. 65, 4799–4807.
3. Kudo, T., Ohkuma, N., Moriya, S., Noda, S. & Ohtoko, K. (1999). Molecular and phylogenetic identification of the intestinal anaerobic microbial community in the hindgut of the termite, *Reticulitermes spermatus*, without cultivation. Extremophiles 2, 151–161.
4. Ward, D. M., Weller, R. & Bateson, M. M. (1990). 16S rRNA sequences reveal numerous uncultured microorganisms in a natural community. Nature 345, 63–65.
5. Bintrim, S. B., Donohue, T. J., Handelsman, J., Roberts, G. P. & Goodman, R. M. (1997). Molecular phylogeny of Archaea from soil. Proc. Natl. Acad. Sci. U.S.A. 94, 277–282.
6. Borneman, J., Skroch, P. W., O Sullivan, -K. M., Palus, J. A., Rumjanek, N. G., Jansen, J. L., Nienhuis, J. & Triplett, E. W. (1996). Molecular microbial diversity of an agricultural soil in Wisconsin. Appl. Environ. Micro biol. 62, 1935–1943.
7. Stackebrandt, B., Liesack, W. & Goebel, B. M. (1993). Bacterial diversity in a soil sample from a subtropical Australian environment as determined by 16S rDNA analysis. FASEB J. 7, 232–236.
8. Handelsman, J., Rondon, M. R., Brady, S. F., Clardy, J. & Goodman, R. M. (1998). Molecular biological access to the chemistry of unknown soil microbes: a new frontier for natural products. Chem. Biol. 5, R245–R249.
9. Shizuya, H., Birren, B., Kim, U. J., Mancino, V., Slepak, Y., Tachiri, Y. & Simon, M.(1992). Cloning and stable maintenance of 300-kilobase-pair fragments of human DNA in *Escherichia coli* using an F-factor-based vector. Proc. Natl. A cad. Sci. U.S.A. 89, 8794–8797.
10. Torsvik, V., Goksoyr, J. & Daae, F. L. (1990). High diversity of DNA of soil bacteria. Appl. Environ. Microbiol. 56, 782–787.
11. Torsvik, V., Salte, K., Sorheim, R. & Goksoyr, J. (1990). Comparison of phenotypic diversity and heterogeneity in a population of soil bacteria. Appl. Environ. Microbiol. 56, 776–781.
12. Liesack, W. & Stackebrandt, E. (1992). Occurrence of novel groups of the domain Bacteria as revealed by analysis ofgenetic material isolated from an Australian terrestrial environment. J. Bacteriol. 174, 5072–5078.
13. Hugenholtz, P., Goebel B. M. & Pace, N. R. (1998). Impact of culture-independent studies on the emerging phylogenetic view of bacterial diversity. J. Bacteriol. 180, 4765–4774.
14. Zhou, J., Bruns, M. A. & Tiedje, J. M. (1996). DNA recovery from soils of diverse composition. Appl. Environ. Microbiol. 62, 316–322.
15. Rondon, M. R., August, P. R., Betterman, A. D., Brady, S. F., Grossman, T. H., Liles, M. R., Loiacono, K. A., Lynch, B. A., MacNeil, I. A., Charles, M., Tiong, C. L., Gilman, M., Osburne, M. S., Clardy, J., Hendelsman, J. & Goodman, R. M. (2000). Cloning the soil metagenome: a strategy for accessing the genetic and functional diversity of uncultured microorganisms. Appl. Environ. Microbiol., 66 in press.
16. Gibson, L. F. & George, A. M. (1998). Melanin and novel precursors from Aeromonas media. FEMS Microbiol. Lett. 169, 261–268. (and references therein).
17. Schmidt, R., Krein, R. & Regnier, M. (1996). The use of diethylaminoethylcellulose membrane filters in a bioassay to quantify melanin synthesis. Anal. Biochem. 235, 113–118.
18. Budzikiwicz, H., Eckau, H. & Ehrenberg, M. (1972). Bis (3-indolyl-)-3H-indolyliden-methan, em von *Saccharomyces Cerevisiae* Gebildeter Farbstoff Tetrahedron Lett. 36, 3807–3810.

19. Stupnikova, T. V., Rybenko, L. A., Skorobogatova, Z. M. & Sheinkman, A. K. (1978). Tris(3-indoyl)methyl perchlorates as new dyes of the triarylmethane series. Khim. Geterotsikl. Soedin. 3, 416.
20. Chang, T. M., Chuang, Y. C., Su, J. H. & Chang, M. C. (1997). Cloning and sequence analysis of a novel hemolysin gene (vllY) from *Vibrio vulnificus*. Appl. Environ. Microbiol. 63, 3851–3857.
21. Fuqua, W. C., Coyne, V. E., Stein, D. C., Lin, C. M. & Weiner, R. M. (1991). Characterization of melA: a gene encoding melanin biosynthesis from the marine bacterium *Shewanella colwelliana*. Gene, 109, 131–136.
22. Milcamps, A & de Bruijn, F. J. (1999). Identification of a novel nutrient-deprivationinduced *Sinorhizobium meliloti* gene (hmgA) involved in the degradation of tyrosine. Microbiology 145, 935–947.
23. Redenbach, M., Kieser, H. M., Denapaite, D., Eichner, A., Cullum, J., Kinashi, H. & Hopwood, D. A. (1996). A set of ordered cosmids and a detailed genetic and physical map for the 8 Mb *Streptomyces coelicolor* A3(2) chromosome. Mol. Microbiol. 21, 77–96.
24. Fernandez-Canon, J. M. & Penalva, M. A. (1995). Molecular characterization of a gene encoding a homogentisate dioxygenase from *Aspergillus nidulans* and identification of its human and plant homologues. J. Biol. Chem. 270, 21199–21205.
25. Wintermeyer, E., Flugel, M., Ott, M., Steinert, M., Rdest, U., Mann, K. H. & Hacker, J. (1994). Sequence determination and mutational analysis of the lly locus of *Legionella pneumophila*. Infect. Immun. 62, 1109–1117.
26. Sambrook, J., Fritsch, E. F. & Maniatis, T. (1989). Molecular Cloning: A Laboratory Manural. (2nd ed.), Cold Spring Harbor Laboratory Press, Cold Spring Harbor, N.Y.
27. Altschul, S. F., Gish, W., Miller, W., Myers, E. W. & Lipman, D. J. (1990). Basic local alignment search tool. J. Mol. Biol. 215, 403–410.
28. Saiki, R. K., Gelfand, D. H., Stoffel, S., Scharf, S. J., Higuchi, R., Horn, G. T., Mullis, K. B. & Erlich, H. A. (1988). Primer-directed enzymatic amplification of DNA with a thermostable DNA polymerase. Science 239, 487–491.
29. Dhingra, O. D. & Sinclair, J. B. (1985). Basic plant pathology methods. Boca Raton, Fla.; CRC Press, Inc., p 308.

What is claimed is:

1. A method of treating bacterial or fungal infection in a subject in need thereof, the method comprising administering to the subject an antibiotic- or antifungal-effective amount of a compound selected from the group consisting of:

wherein each R is independently selected from the group consisting of hydrogen, halo, hydroxy, amino, unsubstituted $C_1$ to $C_6$-alkyl, and $C_1$ to $C_6$-alkyl substituted with one or more of halo, hydroxy, or amino; and $R^1$ is selected from the group consisting of hydrogen, halo, amino, unsubstituted $C_1$ to $C_6$-alkyl, and $C_1$ to $C_6$-alkyl substituted with one or more of halo, hydroxy, or amino; and pharmaceutically-acceptable salts thereof; in combination with a pharmaceutically-acceptable carrier.

2. The method of claim 1, wherein a compound wherein each R is independently selected from the group consisting of hydrogen, halo, hydroxy, and unsubstituted $C_1$ to $C_6$-alkyl is administered to the subject.

3. A method of treating bacterial or fungal infection in a subject in need thereof, the method comprising administering to the subject an antibiotic- or antifungal-effective amount of a compound of formula:

in combination with a pharmaceutically-acceptable carrier.

4. The method of claim 1, wherein the compound is administered to a human subject.

5. The method of claim 1, wherein the bacterial or fungal infection treated is selected from the group consisting of *Erwinia herbicola, Escherichia coli, Salmonella typhimurium, Bacillus cereus, Bacillus subtilis, Staphylococcus aureus, Streptococcus pyogenes, Streptomyces griseus,* and *Candida guilliermondii.*

* * * * *

UNITED STATES PATENT AND TRADEMARK OFFICE
CERTIFICATE OF CORRECTION

PATENT NO. : 7,115,753 B2
APPLICATION NO. : 10/637280
DATED : October 3, 2006
INVENTOR(S) : Handelsman et al.

It is certified that error appears in the above-identified patent and that said Letters Patent is hereby corrected as shown below:

Col. 28, Line 55

1. A method of treating bacterial or fungal infection in a subject in need thereof, the method comprising administering to the subject an antibiotic- or antifungal-effective amount of a compound selected from the group consisting of:

Please remove

And replace with

UNITED STATES PATENT AND TRADEMARK OFFICE
CERTIFICATE OF CORRECTION

PATENT NO. : 7,115,753 B2
APPLICATION NO. : 10/637280
DATED : October 3, 2006
INVENTOR(S) : Handelsman et al.

It is certified that error appears in the above-identified patent and that said Letters Patent is hereby corrected as shown below:

wherein each R is independently selected from the group consisting of hydrogen, halo, hydroxy, amino, unsubstituted $C_1$ to $C_6$-alkyl, and $C_1$ to $C_6$-alkyl substituted with one or more of halo, hydroxy, or amino; and $R^1$ is selected from the group consisting of hydrogen, halo, ~~amino,~~ unsubstituted $C_1$ ~~to $C_6$~~-alkyl, halo-substituted $C_1$-alkyl, unsubstituted $C_2$ to $C_6$-alkyl, and ~~$C_1$~~ $C_2$ to $C_6$-alkyl substituted with one or more of halo, hydroxy, amino; and pharmaceutically-acceptable salts thereof; in combination with a pharmaceutically acceptable carrier.

Signed and Sealed this

Twenty-third Day of January, 2007

JON W. DUDAS
*Director of the United States Patent and Trademark Office*